(12) United States Patent
Myung

(10) Patent No.: US 10,857,017 B2
(45) Date of Patent: Dec. 8, 2020

(54) STENT INSERTION DEVICE FOR CONNECTING HUMAN DIGESTIVE ORGANS

(71) Applicant: BCM Co., Ltd., Gyeonggi-do (KR)

(72) Inventor: Byung Cheol Myung, Gyeonggi-do (KR)

(73) Assignee: BCM Co., Ltd., Gyeonggi-do (KR)

( * ) Notice: Subject to any disclaimer, the term of this patent is extended or adjusted under 35 U.S.C. 154(b) by 171 days.

(21) Appl. No.: 16/199,094

(22) Filed: Nov. 23, 2018

(65) Prior Publication Data

US 2019/0091052 A1   Mar. 28, 2019

(51) Int. Cl.
*A61F 2/966* (2013.01)
*A61F 2/04* (2013.01)
(Continued)

(52) U.S. Cl.
CPC .......... *A61F 2/966* (2013.01); *A61B 17/1114* (2013.01); *A61B 18/082* (2013.01); *A61B 18/1477* (2013.01); *A61B 18/1492* (2013.01); *A61F 2/04* (2013.01); *A61B 2017/1139* (2013.01); *A61B 2018/00494* (2013.01); *A61B 2018/00535* (2013.01); *A61B 2018/00601* (2013.01); *A61B 2018/1427* (2013.01); *A61B 2090/08021* (2016.02); *A61F 2/82* (2013.01); *A61F 2/9517* (2020.05);
(Continued)

(58) Field of Classification Search
CPC .... A61F 2/966; A61F 2/04; A61F 2/82; A61F 2002/9665; A61F 2002/9511; A61F 2/9517; A61F 2002/044; A61F 2002/045; A61F 2002/047; A61F 2002/828; A61B 18/1492; A61B 17/1114; A61B 18/082; A61B 18/1477; A61B 2018/00601; A61B 2017/1139; A61B 2018/1427; A61B 2018/00535; A61B 2090/08021; A61B 2018/00494
See application file for complete search history.

(56) References Cited

U.S. PATENT DOCUMENTS 6,616,675 B1 * 9/2003 Evard .................. A61B 1/3137
606/153
7,115,136 B2 * 10/2006 Park ..................... A61B 17/083
606/155
(Continued)

FOREIGN PATENT DOCUMENTS

KR         100822045        4/2008

*Primary Examiner* — Phong Son H Dang
(74) *Attorney, Agent, or Firm* — IP & T Group LLP

(57) ABSTRACT

A stent insertion device for connecting human digestive organs includes a first handle being connected to one side of an outer tube, the first handle including a first inner passage communicating with the outer tube, a second handle being connected to a first side of an inner tube, the second handle including a second inner passage communicating with the inner tube, wherein a mounting space is provided between the outer tube and the inner tube at a second side of the inner tube, a stent for connecting human digestive organs being compressed and mounted to the mounting space, a third handle being connected to a first side of an insulation tube, the third handle including a third inner passage communicating with the insulation tube, and a needle knife being connected to a second side of the insulation tube.

2 Claims, 6 Drawing Sheets

(51) Int. Cl.
- *A61B 17/11* (2006.01)
- *A61B 18/14* (2006.01)
- *A61B 18/08* (2006.01)
- *A61F 2/82* (2013.01)
- *A61F 2/95* (2013.01)
- *A61B 90/00* (2016.01)
- *A61B 18/00* (2006.01)

(52) U.S. Cl.
CPC ... *A61F 2002/044* (2013.01); *A61F 2002/045* (2013.01); *A61F 2002/047* (2013.01); *A61F 2002/828* (2013.01); *A61F 2002/9511* (2013.01); *A61F 2002/9665* (2013.01)

(56) References Cited

U.S. PATENT DOCUMENTS

| | | | |
|---|---|---|---|
| 7,426,929 B2 * | 9/2008 | Tanaka | A61F 2/04 128/200.24 |
| 7,740,640 B2 * | 6/2010 | Ginn | A61B 17/0057 606/142 |
| 7,780,686 B2 * | 8/2010 | Park | A61B 17/083 606/153 |
| 7,828,814 B2 * | 11/2010 | Brenneman | C09K 8/5753 606/151 |
| 8,070,826 B2 * | 12/2011 | Ginn | A61B 17/0057 623/23.72 |
| 8,398,676 B2 * | 3/2013 | Roorda | A61B 17/0057 606/213 |
| 8,425,539 B2 * | 4/2013 | Binmoeller | A61B 1/00147 606/153 |
| 8,454,632 B2 * | 6/2013 | Binmoeller | A61B 17/11 606/151 |
| 9,486,191 B2 * | 11/2016 | Gianotti | A61B 17/04 |
| 10,004,509 B2 * | 6/2018 | Todd | A61B 17/1114 |
| 2001/0025643 A1 * | 10/2001 | Foley | A61F 2/82 128/898 |
| 2001/0044631 A1 * | 11/2001 | Akin | A61F 2/064 606/153 |
| 2003/0032967 A1 * | 2/2003 | Park | A61B 17/11 606/153 |
| 2003/0120292 A1 * | 6/2003 | Park | A61B 17/1114 606/153 |
| 2005/0075655 A1 * | 4/2005 | Bumbalough | A61B 17/1114 606/153 |
| 2006/0052821 A1 * | 3/2006 | Abbott | A61B 17/064 606/213 |
| 2006/0217761 A1 * | 9/2006 | Opolski | A61B 17/0057 606/213 |
| 2006/0282106 A1 * | 12/2006 | Cole | A61B 17/0643 606/153 |
| 2007/0073337 A1 * | 3/2007 | Abbott | A61B 17/12122 606/213 |
| 2007/0078504 A1 * | 4/2007 | Mialhe | A61B 17/12109 623/1.11 |
| 2008/0243151 A1 * | 10/2008 | Binmoeller | A61B 1/041 606/153 |
| 2009/0024149 A1 * | 1/2009 | Saeed | A61B 17/08 606/151 |
| 2009/0281557 A1 * | 11/2009 | Sander | A61B 17/11 606/151 |

* cited by examiner

STENT INSERTION DEVICE FOR CONNECTING HUMAN DIGESTIVE ORGANS

BACKGROUND OF THE INVENTION

Field of the Invention

The present invention generally relates to a stent insertion device for connecting human digestive organs. More particularly, the present invention relates to a stent insertion device for connecting human digestive organs, whereby the stent insertion device connects the stomach to the biliary duct such that digestive enzymes of the liver and the pancreas or abscesses caused due to a lesion part are moved upward by osmotic pressure when the lesion part having stenosis or blockage occurs at a portion of the biliary duct adjacent to the duodenum.

Description of the Related Art

Generally, when a lesion part having stenosis or blockage occurs in a lumen of a human body such as the esophagus, the duodenum, the biliary tract, the urethra, or a urinary organ, the proper function of the lumen moving a body fluid is deteriorated.

Accordingly, according to a conventional method, a stent is inserted into a lesion part having stenosis or blockage by an insertion device so as to expand a stenotic lumen.

In this regard, patent document 1 provides a stent insertion device for operating on a stenotic portion of a human body, wherein a push rod is configured to be inserted into an outer tube connected to a handle body from a rear side of the outer tube and protrude to a front side of the outer tube, and a mounting tube is provided at a front end of the push rod, a rear end part of the mounting tube being inserted into a front end of the outer tube while the stent having a reduced volume is inserted into and mounted to the mounting tube, whereby the stent is gradually expanded to be restored to an initial state thereof from a rear end thereof to a front end thereof by the push rod pushing the mounting tube.

However, presently, a stent insertion device is required that connects the stomach to the biliary duct such that digestive enzymes of the liver and the pancreas or abscesses caused due to the lesion part are prevented from stagnating in the biliary duct when the lesion part having stenosis or blockage occurs at a portion of the biliary duct adjacent to the duodenum.

DOCUMENT OF RELATED ART (Patent Document 1) Korean Patent No. 10-0822045 (registered on Apr. 7, 2008)

SUMMARY OF THE INVENTION

Accordingly, the present invention has been made keeping in mind the above problems occurring in the related art, and the present invention is intended to propose a stent insertion device for connecting human digestive organs, wherein the stent insertion device connects the stomach to the biliary duct such that digestive enzymes of the liver and the pancreas or abscesses caused due to the lesion part are moved upward by osmotic pressure when the lesion part having stenosis or blockage occurs at a portion of the biliary duct adjacent to the duodenum.

In order to achieve the above object, according to one aspect of the present invention, there is provided a stent insertion device for connecting human digestive organs, the stent insertion device including: a first handle being connected to one side of an outer tube, the first handle including a first inner passage communicating with the outer tube, a second handle being connected to a first side of an inner tube moveably inserted into the outer tube and the first inner passage, the second handle including a second inner passage communicating with the inner tube, wherein a mounting space is provided between the outer tube and the inner tube at a second side of the inner tube, a stent for connecting human digestive organs being compressed and mounted to the mounting space, a third handle being connected to a first side of an insulation tube moveably inserted into the inner tube and the second inner passage, the third handle including a third inner passage communicating with the insulation tube, and a needle knife being connected to a second side of the insulation tube, the needle knife including a fourth inner passage communicating with the insulation tube and protruding from the outer and inner tubes during hole forming operations on a stomach and a biliary duct.

According to the present invention, the hole forming operations on the stomach and the biliary duct are quickly performed by a piercing force and high-frequency heat of the needle knife.

Furthermore, since holes are formed on the stomach and the biliary duct by a piercing force and high-frequency heat of the needle knife, incisions on the stomach and the biliary duct are not required.

In addition, a guide wire prevents outer and inner tubes and the insulation tube from being bent so as to improve straightness thereof, whereby the outer and inner tubes and the insulation tube quickly move forward/rearward depending on an operation condition.

That is, a mounting operation of the stent for connecting human digestive organs is quickly performed so as to relieve a physical burden of a patient.

According to the present invention, after the hole forming operations on the stomach and the biliary duct are completed, the needle knife is inserted into the inner tube by the third handle moving rearward.

That is, after the hole forming operations on the stomach and the biliary duct are completed, the needle knife is prevented from needlessly pricking the biliary duct, and an inner surface of the biliary duct is prevented from needlessly being burned by high-frequency heat produced in the needle knife.

BRIEF DESCRIPTION OF THE DRAWINGS

The above and other objects, features and other advantages of the present invention will be more clearly understood from the following detailed description when taken in conjunction with the accompanying drawings, in which.

DETAILED DESCRIPTION OF THE INVENTION

Hereinbelow, an exemplary embodiment of the present invention will be described in detail with reference to the accompanying drawings.

Figure 1:
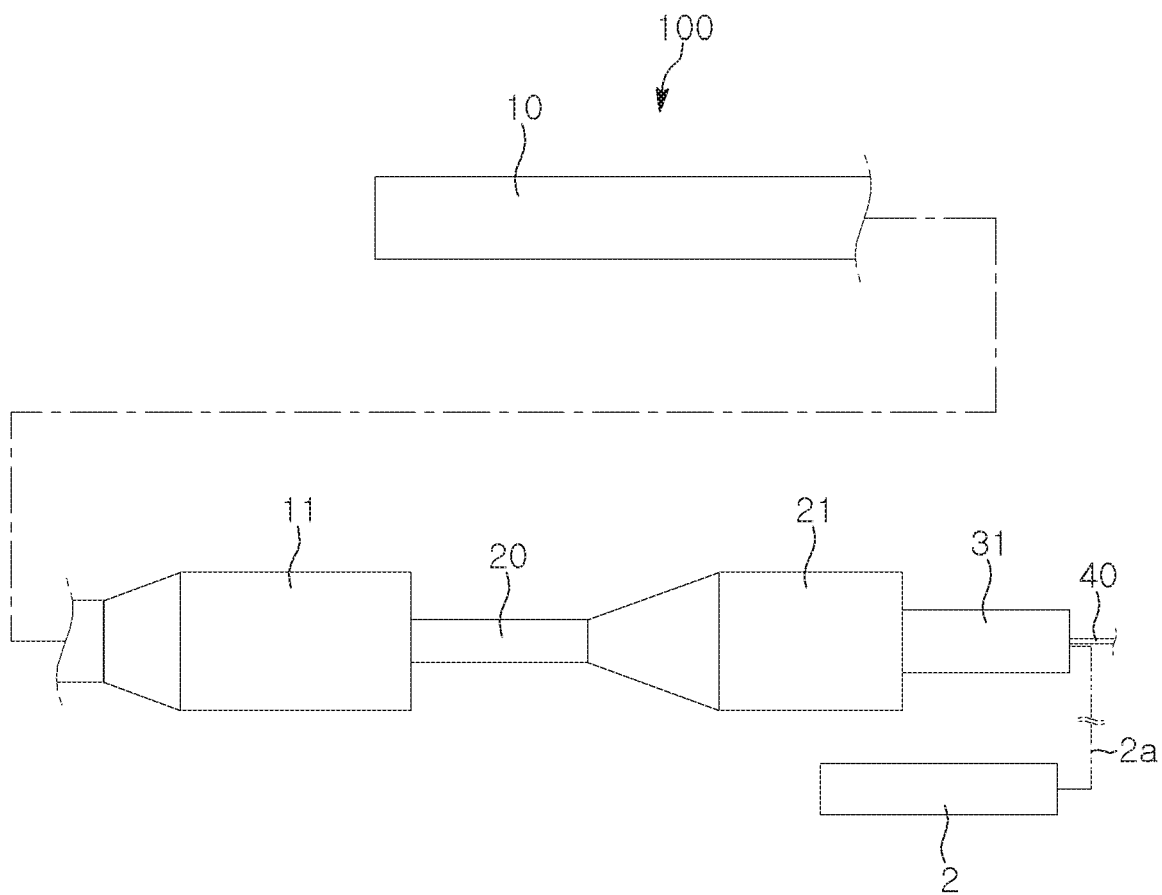
FIG. 1 is a view of a stent insertion device for connecting human digestive organs according to an embodiment of the present invention.
Figure 2A:
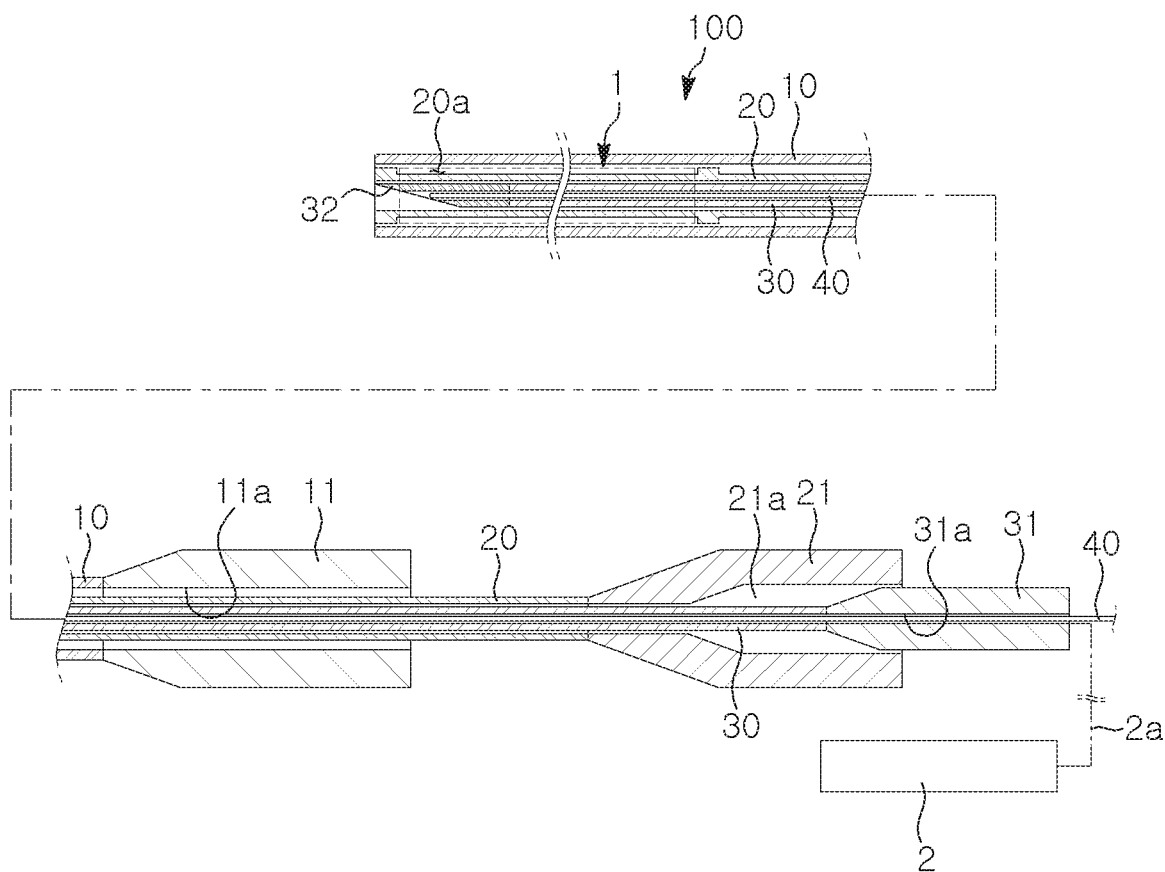
FIGS. 2a and 2b are sectional views of FIG. 1.
Figure 2B:
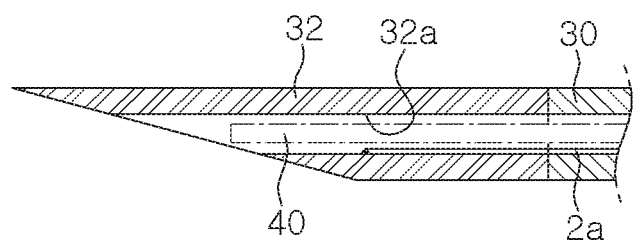
Figure 3A:
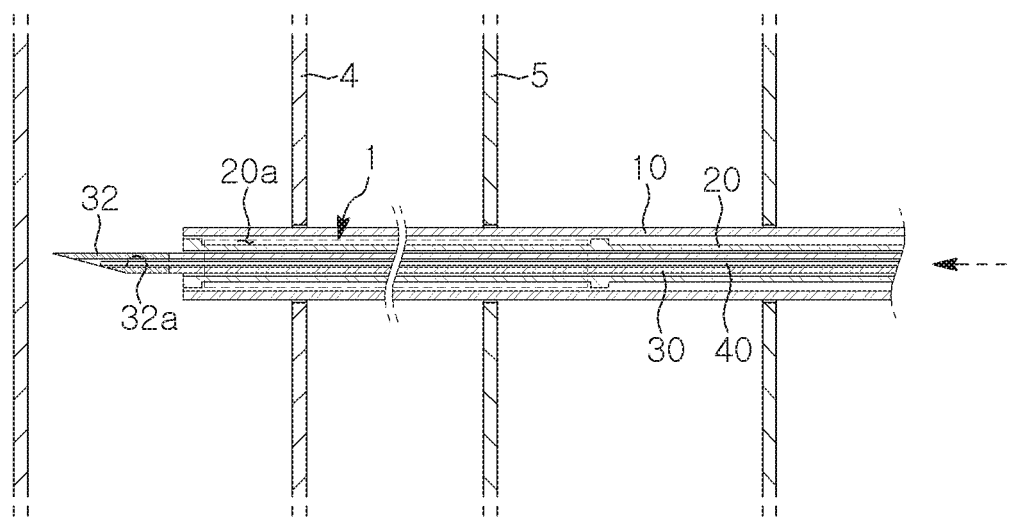
FIGS. 3a, 3b, 4a, 4b, 5a, 5b, 6a, 6b, and 7 are operation state views of the stent insertion device according to the embodiment of the present invention.
Figure 3B:
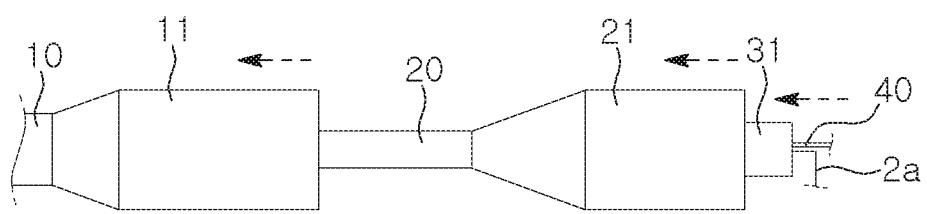
Figure 4A:
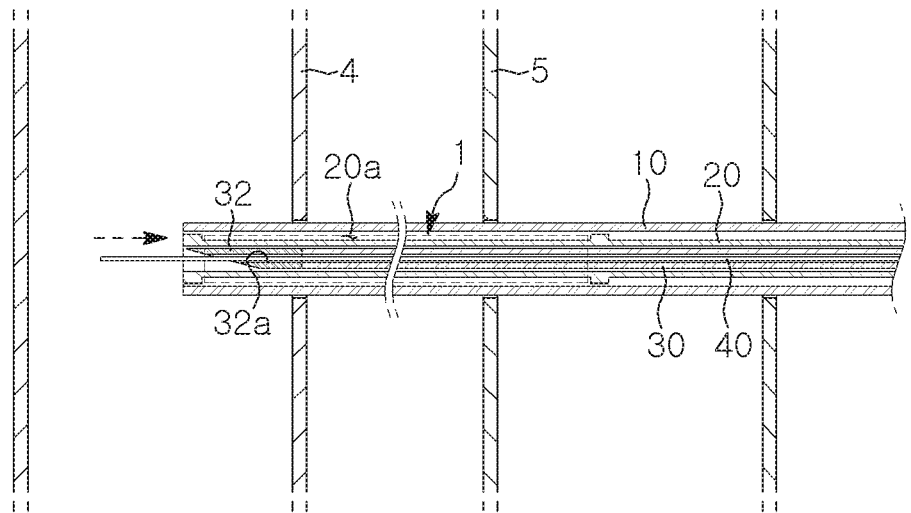
Figure 4B:
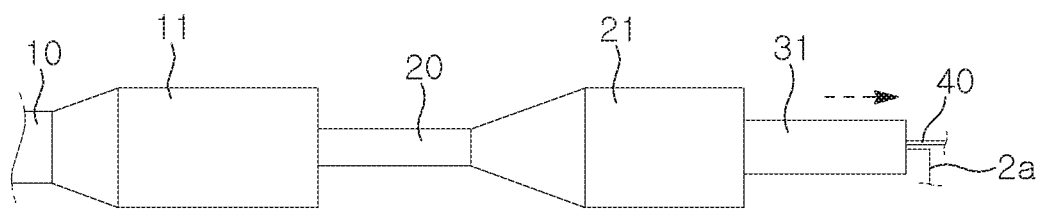
Figure 5A:
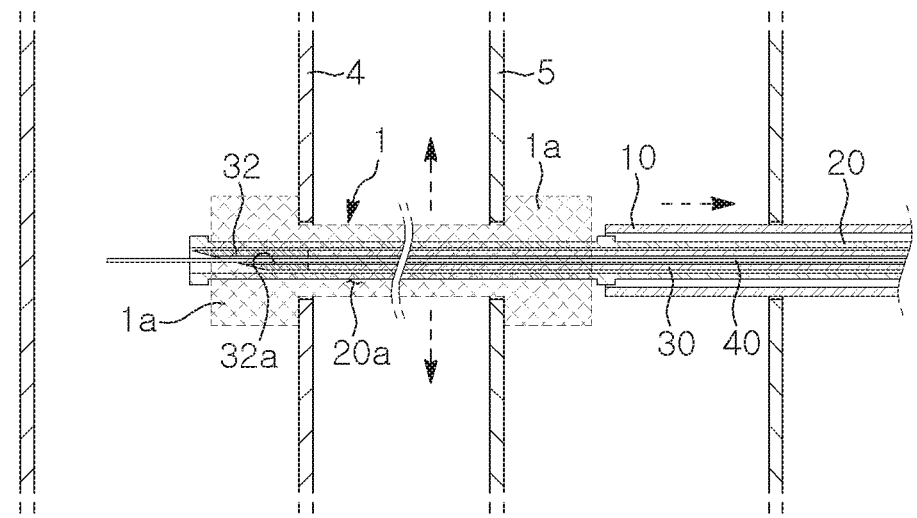
Figure 5B:
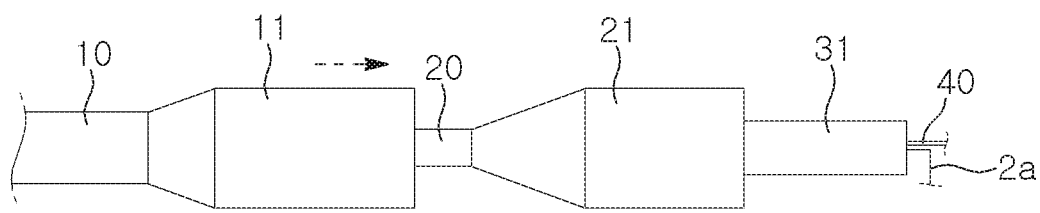
Figure 6A:
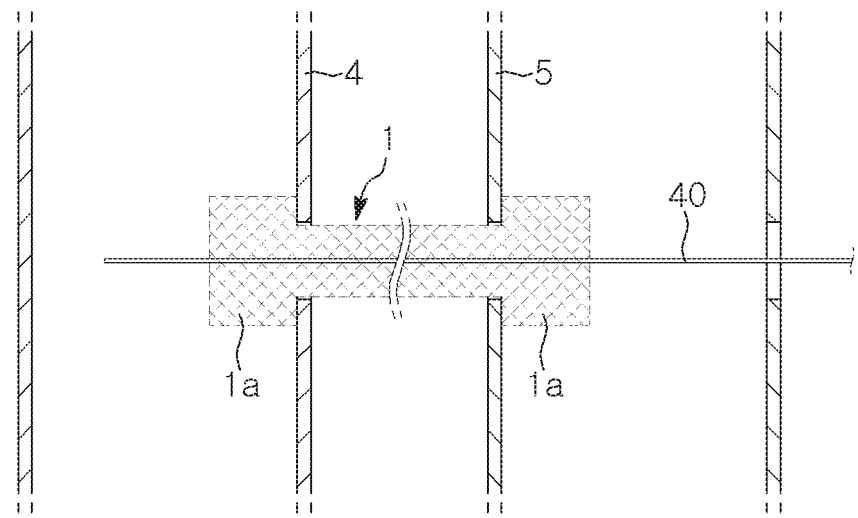
Figure 6B:
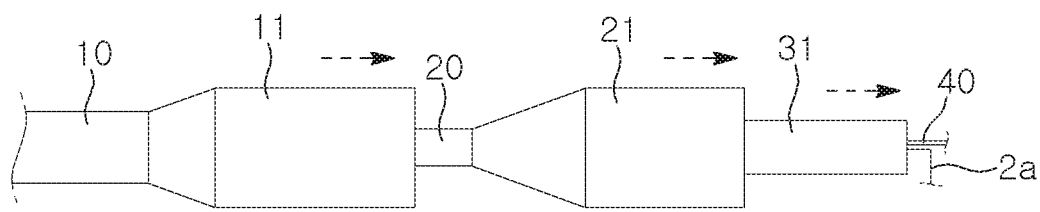
Figure 7:
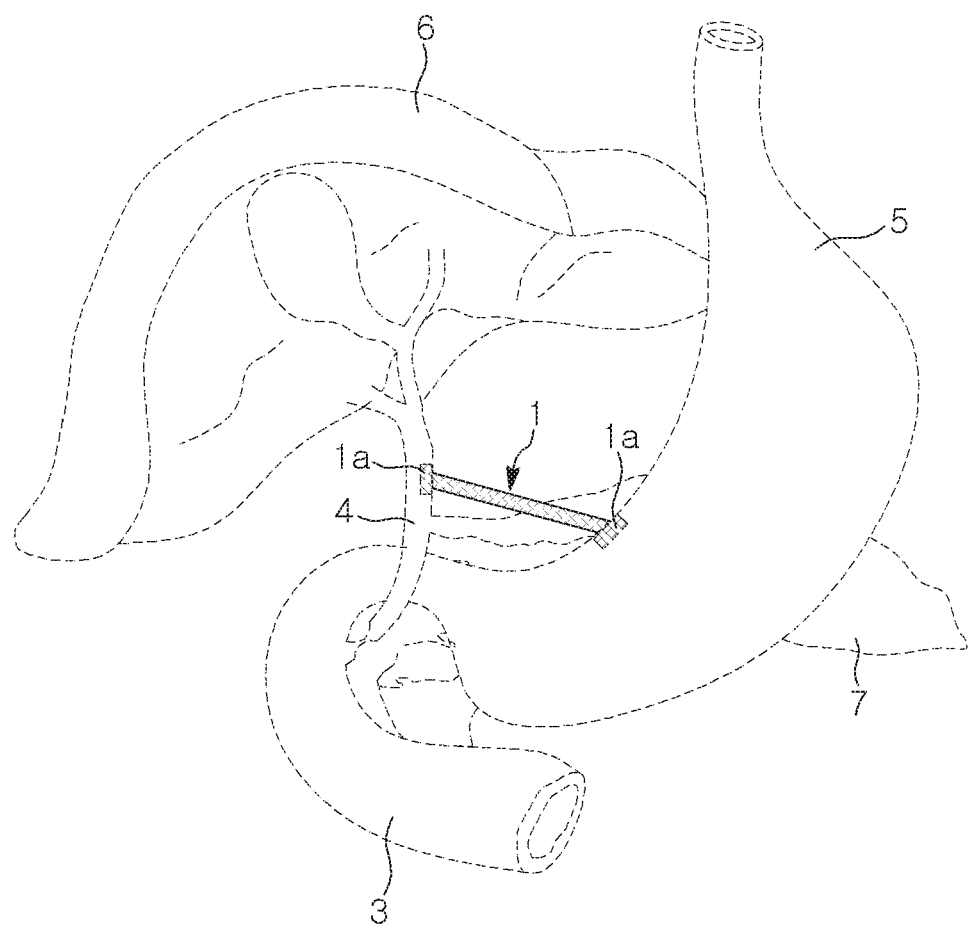

As shown in FIGS. 1 to 7, a stent insertion device 100 for connecting human digestive organs according to the embodiment of the present invention is used when a stent 1 for connecting human digestive organs is mounted so as to connect the biliary duct 4 and the stomach 5 to each other when a lesion part having stenosis or blockage occurs at a portion of the biliary duct 4 adjacent to the duodenum 3.

That is, the stent insertion device 100 for connecting human digestive organs is used when the stent 1 for connecting human digestive organs is mounted such that digestive enzymes of the liver 6 and the pancreas 7 or abscesses caused due to the lesion part are moved to the stomach 5 by osmotic pressure.

In addition, the stent insertion device 100 for connecting human digestive organs includes an outer tube 10 and a first handle 11 connected to one side of the outer tube 10.

Here, the first handle 11 includes a first inner passage 11a provided therein communicating with the outer tube 10.

Furthermore, the stent insertion device 100 for connecting human digestive organs includes an inner tube 20 moveably inserted into the outer tube 10 and the first inner passage 11a and a second handle 21 being connected to a first side of the inner tube 20.

Here, the second handle 21 includes a second inner passage 21a communicating with the inner tube 20, and a mounting space 20a is provided between the outer tube 10 and the inner tube 20 at a second side of the inner tube 20, the stent 1 for connecting human digestive organs being compressed and mounted to the mounting space.

In addition, the stent insertion device 100 for connecting human digestive organs includes an insulation tube 30 moveably inserted into the inner tube 20 and the second inner passage 21a, and a third handle 31 connected to a first side of the insulation tube 30.

Here, the third handle 31 includes a third inner passage 31a provided therein communicating with the insulation tube 30, and a needle knife 32 is connected to a second side of the insulation tube 30 and protrudes from the outer and inner tubes 10, 20 during hole forming operations on the stomach 5 and the biliary duct 4.

In addition, the needle knife 32 includes a fourth inner passage 32a provided therein communicating with the insulation tube 30 and is connected to an electric wire 2a of a high frequency generator 2 inserted into the third inner passage 31a, the insulation tube 30, and the fourth inner passage 32a.

Furthermore, the stent insertion device 100 for connecting human digestive organs includes a guide wire 40 moveably inserted into the third inner passage 31a, the insulation tube 30, and the fourth inner passage 32a.

In addition, the stent 1 for connecting human digestive organs includes expanded tube parts 1a protruding from opposite sides thereof and coated with medical membranes having affinity with the human body.

According to the embodiment of the present invention, the operation and effect of the stent insertion device 100 for connecting human digestive organs, which has above-mentioned configuration, will be described hereinafter.

As shown in FIGS. 1 to 7, when the lesion part having stenosis or blockage occurs at a portion of the biliary duct 4 adjacent to the duodenum 3, a portion of a human body surface is cut, and an endoscope and the outer tube 10 are pushed through the cut part and inserted into the human body.

Here, the needle knife 32 does not protrude from the outer and inner tubes 10, 20, the guide wire 40 is inserted into the third inner passage 31a, the insulation tube 30, and the fourth inner passage 32a, and the stent 1 for connecting human digestive organs is compressed and mounted to the mounting space 20a defined between the outer tube 10 and the inner tube 20.

In addition, when an operation position of the stomach 5 is checked by the endoscope, the outer tube 10 is located at the operation position of the stomach 5.

Next, after the needle knife 32 is exposed from the outer and inner tubes 10, 20 by the third handle 31 moving forward, the high frequency generator 2 is operated such that electric current is supplied to the needle knife 32 via the electric wire 2a.

Accordingly, high-frequency heat is produced in the needle knife 32.

Next, the needle knife 32 pierces the stomach 5 and the biliary duct 4 so as to form holes thereon by the first, second, and third handles 11, 21, 31 and the guide wire 40 moving forward together from the stomach 5 to the biliary duct 4.

Here, while positions of holes to be formed on the stomach 5 and the biliary duct 4 are burned by high-frequency heat produced in the needle knife 32, the holes are formed by a piercing force of the needle knife 32.

Furthermore, since the guide wire 40 supports the outer and inner tubes 10, 20 and the insulation tube 30 during the hole forming operations on the stomach 5 and the biliary duct 4 by the needle knife 32, the outer and inner tubes 10, 20 and the insulation tube 30 moving forward are not bent.

In addition, after the hole forming operations on the stomach 5 and the biliary duct 4 are completed, an operation of the high frequency generator 2 stops while the needle knife 32 positioned in the binary duct 4 is inserted into the inner tube 20 by the third handle 31 moving rearward.

Here, the third handle 31 is moved rearward along the guide wire 40 inserted into the third inner passage 31a, and the insulation tube 30 is also moved rearward along the inserted guide wire 40.

Next, the outer tube 10 is moved rearward until the stent 1 compressed to be mounted to the mounting space 20a of the inner tube 20 is expanded to an initial state by the first handle 11 moving rearward.

Here, the first handle 11 is moved rearward along the inner tube 20 inserted into the first inner passage 11a, and the outer tube 10 is also moved rearward along the inserted inner tube 20.

Accordingly, while the stent 1 for connecting human digestive organs is fitted to holes formed on the stomach 5 and the biliary duct 4, the expanded tube parts 1a of the stent 1 are held on positions neighboring the holes.

That is, the stomach 5 and the biliary duct 4 are connected to each other by the stent 1 for connecting human digestive organs.

Next, the first, second, and third handles 11, 21, 31 are moved rearward such that the outer and inner tubes 10, 20, the insulation tube 30, and the needle knife 32 are escaped from a human body.

Here, since the guide wire 40 inserted into the third inner passage 31a, the insulation tube 30, and the fourth inner passage 32a supports the outer and inner tubes 10, 20 and the insulation tube 30, the outer and inner tubes 10, 20 and the insulation tube 30 moving rearward are not bent.

In addition, a mounting operation of the stent 1 for connecting human digestive organs is completed by the guide wire 40 moving rearward to escape from the human body.

Accordingly, digestive enzymes of the liver 6 and the pancreas 7 do not stagnate in the lesion part having stenosis or blockage occurring at a portion of the biliary duct 4 adjacent to the duodenum 3 and are moved from the biliary duct 4 to the stomach 5 through the stent 1 for connecting human digestive organs by the osmotic pressure.

That is, food digestion performed in the duodenum 3 by digestive enzymes of the liver 6 and the pancreas 7 is performed in the stomach 5.

In addition, abscesses caused due to the lesion part are moved to the stomach 5 by the osmotic pressure and do not stagnate in the lesion part having stenosis or blockage occurring at a portion of the biliary duct 4 adjacent to the duodenum.

Meanwhile, when the stent insertion device 100 does not require high-frequency heat during the hole forming operations on the stomach 5 and the biliary duct 4, that is, during a nonelectric operation, the high frequency generator 2 is not operated such that an electric current is not supplied to the needle knife 32 by the electric wire 2a.

That is, an operation is performed only by a piercing force of the needle knife 32 without the high-frequency heat.

Although a preferred embodiment of the present invention has been described for illustrative purposes, those skilled in the art will appreciate that various modifications, additions and substitutions are possible, without departing from the scope and spirit of the invention as disclosed in the accompanying claims.

What is claimed is:

1. A stent insertion device for connecting human digestive organs, the stent insertion device comprising:
    a first handle being connected to one side of an outer tube, the first handle including a first inner passage communicating with the outer tube;
    second handle being connected to a first side of an inner tube moveably inserted into the outer tube and the first inner passage, the second handle including a second inner passage communicating with the inner tube,
    wherein a mounting space is provided between the outer tube and the inner tube at a second side of the inner tube, a stent for connecting human digestive organs being compressed and mounted to the mounting space;
    a third handle being connected to a first side of an insulation tube moveably inserted into the inner tube and the second inner passage, the third handle including a third inner passage communicating with the insulation tube; and
    a needle knife being connected to a second side of the insulation tube, the needle knife including a fourth inner passage communicating with the insulation tube and protruding from the outer and inner tubes during hole forming operations on a stomach and a biliary duct wherein the needle knife is inserted into the inner tube by the third handle moving rearward after the hole forming operation on the stomach and the biliary duct are completed.

2. The stent insertion device of claim 1, wherein a guide wire is provided to be moveably inserted into the third inner passage, the insulation tube, and the fourth inner passage.

* * * * *